(12) United States Patent
Cheng et al.

(10) Patent No.: US 12,364,423 B2
(45) Date of Patent: Jul. 22, 2025

(54) AUTOMATED URINARY OUTPUT-MEASURING SYSTEMS AND METHODS

(71) Applicant: C. R. Bard, Inc., Franklin Lakes, NJ (US)

(72) Inventors: Jason Jishen Cheng, Avondale Estates, GA (US); Audrey Earnshaw, Erie, CO (US); Trevor Dimicco, Providence, RI (US); Juan C. Tapia, Larenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 294 days.

(21) Appl. No.: 17/556,931

(22) Filed: Dec. 20, 2021

(65) Prior Publication Data
US 2022/0192566 A1    Jun. 23, 2022

Related U.S. Application Data

(60) Provisional application No. 63/128,558, filed on Dec. 21, 2020.

(51) Int. Cl.
*A61B 5/20* (2006.01)
*A61B 5/00* (2006.01)
(Continued)

(52) U.S. Cl.
CPC ............ *A61B 5/208* (2013.01); *A61B 5/0004* (2013.01); *A61B 5/6807* (2013.01);
(Continued)

(58) Field of Classification Search
CPC ..... A61B 5/0004; A61B 5/208; A61B 5/6807; A61B 5/7246; A61B 10/007; A61B 2562/0219; G01F 22/00; G01F 23/2962
See application file for complete search history.

(56) References Cited

U.S. PATENT DOCUMENTS 3,661,143 A    5/1972   Henkin
3,781,920 A    1/1974   Browne et al.
(Continued)

FOREIGN PATENT DOCUMENTS

CA    2882654 A1    10/2007
CN    2445749 Y     9/2001
(Continued)

OTHER PUBLICATIONS

"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).*

(Continued)

*Primary Examiner* — Alex M Valvis
*Assistant Examiner* — Anna Roberts
(74) *Attorney, Agent, or Firm* — Rutan & Tucker LLP

(57) ABSTRACT

Disclosed are automated urinary output ("UO")-measuring systems and methods. An automated UO-measuring system can include a container configured to collect a fluid such as urine. The container can include a console, one or more ultrasonic sensors coupled to the console for determining a fluid level within the container, one or more accelerometers coupled to the console for determining a near-zero acceleration state of the container for the determining of the fluid level within the container, and a valve configured to pass fluid therethrough by way of a fluid line coupled to the valve. The automated UO-measuring system can also include a container holder. The container holder can have a pocket for holding the container and a sleeve for securing the container to a user. A method of the automated UO-measuring system can include a method of using the automated UO-measuring system to collect and measure urine output of the user.

21 Claims, 7 Drawing Sheets

(51) Int. Cl.
*A61B 10/00* (2006.01)
*G01F 22/00* (2006.01)

(52) U.S. Cl.
CPC .......... *A61B 5/7246* (2013.01); *A61B 10/007* (2013.01); *G01F 22/00* (2013.01); *A61B 2562/0219* (2013.01)

(56) References Cited

U.S. PATENT DOCUMENTS

| | | |
|---|---|---|
| 3,851,650 A | 12/1974 | Darling |
| 3,919,455 A | 11/1975 | Sigdell et al. |
| 4,276,889 A | 7/1981 | Kuntz et al. |
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A | 8/1982 | Jespersen |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,712,567 A | 12/1987 | Gille et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,146,637 A | 9/1992 | Bressler et al. |
| 5,409,014 A | 4/1995 | Napoli et al. |
| 5,586,085 A | 12/1996 | Lichte |
| 5,725,515 A | 3/1998 | Propp |
| 5,733,319 A | 3/1998 | Neilson et al. |
| 5,738,656 A | 4/1998 | Wagner |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A | 4/1999 | Han et al. |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,256,532 B1 | 7/2001 | Cha |
| 6,261,254 B1 | 7/2001 | Baron et al. |
| 6,434,418 B1 | 8/2002 | Neal et al. |
| 6,579,247 B1 | 6/2003 | Abramovitch et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,161,484 B2 | 1/2007 | Tsoukalis |
| 7,211,037 B2 | 5/2007 | Briggs et al. |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,976,533 B2 | 7/2011 | Larsson |
| 7,998,126 B1 | 8/2011 | Fernandez |
| 8,295,933 B2 | 10/2012 | Gerber et al. |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,374,688 B2 | 2/2013 | Libbus et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,045,887 B2 | 6/2015 | O'Malley |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,592,034 B2 | 3/2017 | Hall et al. |
| 9,642,987 B2 | 5/2017 | Bierman et al. |
| 9,731,097 B2 | 8/2017 | Andino et al. |
| 9,895,095 B2 | 2/2018 | Chen |
| 9,962,516 B2 | 5/2018 | Lampotang et al. |
| 10,182,747 B2 | 1/2019 | Charlez et al. |
| 10,245,008 B2 | 4/2019 | Paige |
| 10,362,981 B2 | 7/2019 | Paz et al. |
| 10,383,606 B1 | 8/2019 | McCord et al. |
| 10,448,875 B2 | 10/2019 | Holt et al. |
| 10,799,386 B1 | 10/2020 | Harrison, Sr. |
| 10,881,778 B2 | 1/2021 | Scarpaci et al. |
| 11,540,760 B2 | 1/2023 | Guillemette |
| 11,703,365 B2 | 7/2023 | Tourchak et al. |
| 2001/0056226 A1 | 12/2001 | Zodnik et al. |
| 2002/0016719 A1 | 2/2002 | Nemeth et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1 | 12/2004 | Anstadt et al. |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0065713 A1 | 3/2006 | Kingery |
| 2006/0100743 A1 | 5/2006 | Townsend et al. |
| 2006/0253091 A1 | 11/2006 | Vernon |
| 2007/0010797 A1 | 1/2007 | Nishtala et al. |
| 2007/0106177 A1 | 5/2007 | Hama |
| 2007/0145137 A1 | 6/2007 | Mrowiec |
| 2007/0225668 A1 | 9/2007 | Otto |
| 2007/0252714 A1 | 11/2007 | Rondoni et al. |
| 2008/0217391 A1 | 9/2008 | Roof et al. |
| 2008/0312550 A1 | 12/2008 | Nishtala et al. |
| 2008/0312556 A1 | 12/2008 | Dijkman |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0064426 A1 | 3/2010 | Chikara Imamura |
| 2010/0094204 A1 | 4/2010 | Nishtala |
| 2010/0130949 A1* | 5/2010 | Garcia ............. A61M 25/0017 604/326 |
| 2010/0137743 A1 | 6/2010 | Nishtala et al. |
| 2011/0113540 A1 | 5/2011 | Plate et al. |
| 2011/0120219 A1 | 5/2011 | Barlesi et al. |
| 2011/0178425 A1 | 7/2011 | Nishtala et al. |
| 2011/0224636 A1* | 9/2011 | Keisic .................. A61F 5/4408 604/328 |
| 2011/0230824 A1 | 9/2011 | Salinas et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0035496 A1 | 2/2012 | Denison et al. |
| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0118650 A1 | 5/2012 | Gill |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1 | 12/2012 | Coston et al. |
| 2012/0323502 A1 | 12/2012 | Tanoura et al. |
| 2013/0066166 A1 | 3/2013 | Burnett et al. |

(56) References Cited

U.S. PATENT DOCUMENTS

| | | |
|---|---|---|
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0187666 A1 | 7/2014 | Aizenberg et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0120321 A1 | 4/2015 | David et al. |
| 2015/0233749 A1 | 8/2015 | Wang et al. |
| 2015/0342576 A1 | 12/2015 | Hall et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0183819 A1 | 6/2016 | Burnett et al. |
| 2017/0035342 A1 | 2/2017 | Elia et al. |
| 2017/0043089 A1 | 2/2017 | Handler |
| 2017/0100068 A1 | 4/2017 | Kostov |
| 2017/0113000 A1 | 4/2017 | Tobescu et al. |
| 2017/0136209 A1* | 5/2017 | Burnett .................. A61M 1/84 |
| 2017/0140103 A1 | 5/2017 | Angelides |
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2017/0322197 A1 | 11/2017 | Hall et al. |
| 2018/0015251 A1 | 1/2018 | Lampotang et al. |
| 2018/0110456 A1 | 4/2018 | Cooper et al. |
| 2018/0160961 A1 | 6/2018 | Gopinathan et al. |
| 2018/0214122 A1 | 8/2018 | Ansell et al. |
| 2018/0214297 A1 | 8/2018 | Hughett et al. |
| 2018/0245967 A1 | 8/2018 | Parker et al. |
| 2018/0280236 A1 | 10/2018 | Ludin et al. |
| 2018/0317891 A1 | 11/2018 | Kim |
| 2018/0344234 A1 | 12/2018 | McKinney et al. |
| 2019/0006047 A1 | 1/2019 | Gorek et al. |
| 2019/0017535 A1 | 1/2019 | Ormsbee et al. |
| 2019/0046102 A1 | 2/2019 | Kushnir et al. |
| 2019/0069829 A1* | 3/2019 | Bulut .................. A61B 5/01 |
| 2019/0069830 A1 | 3/2019 | Holt et al. |
| 2019/0126006 A1 | 5/2019 | Rehm et al. |
| 2019/0150821 A1 | 5/2019 | Waters et al. |
| 2019/0167144 A1 | 6/2019 | Jung et al. |
| 2019/0201596 A1 | 7/2019 | Luxon et al. |
| 2019/0223844 A1 | 7/2019 | Aboagye et al. |
| 2019/0247236 A1 | 8/2019 | Sides et al. |
| 2019/0254582 A1 | 8/2019 | Wei et al. |
| 2019/0321588 A1 | 10/2019 | Burnett et al. |
| 2019/0328945 A1 | 10/2019 | Analytis et al. |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0064172 A1 | 2/2020 | Tabaczewski et al. |
| 2020/0085378 A1 | 3/2020 | Burnett et al. |
| 2020/0187863 A1 | 6/2020 | Tu et al. |
| 2020/0268302 A1 | 8/2020 | Oh |
| 2020/0268303 A1 | 8/2020 | Oliva |
| 2020/0289749 A1 | 9/2020 | Odashima et al. |
| 2020/0405524 A1* | 12/2020 | Gill .................. A61F 5/4408 |
| 2021/0054610 A1 | 2/2021 | Hall et al. |
| 2021/0077007 A1 | 3/2021 | Jouret et al. |
| 2021/0100533 A1 | 4/2021 | Seres et al. |
| 2021/0299353 A1* | 9/2021 | Mannu .................. A61M 5/1723 |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0079487 A1 | 3/2022 | Horiguchi et al. |
| 2022/0192564 A1 | 6/2022 | Kriscovich et al. |
| 2022/0192565 A1 | 6/2022 | Cheng et al. |
| 2022/0193375 A1 | 6/2022 | Rehm et al. |
| 2022/0233120 A1* | 7/2022 | Beuret .................. A61B 5/208 |
| 2022/0296140 A1 | 9/2022 | Nguyen et al. |
| 2022/0330867 A1 | 10/2022 | Conley et al. |
| 2022/0386917 A1 | 12/2022 | Mann et al. |
| 2023/0019703 A1 | 1/2023 | Behzad et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |
| 2024/0042120 A1 | 2/2024 | Cheng et al. |
| 2024/0081708 A1 | 3/2024 | Kelly et al. |
| 2024/0108268 A1 | 4/2024 | Woodard et al. |
| 2024/0252783 A1 | 8/2024 | Waitkus et al. |
| 2024/0347162 A1 | 10/2024 | Meese et al. |
| 2024/0360938 A1 | 10/2024 | Cheng et al. |
| 2024/0424186 A1 | 12/2024 | Justice et al. |
| 2025/0090066 A1 | 3/2025 | Tourchak |
| 2025/0120636 A1 | 4/2025 | Compton et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 103054559 B | 5/2015 |
| CN | 107952140 A | 4/2018 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2437549 A | 10/2007 |
| GB | 2576743 A | 3/2020 |
| JP | S49-75171 A | 7/1974 |
| JP | S54-147066 A | 11/1979 |
| JP | S58-190719 A | 11/1983 |
| JP | S60-219517 A | 11/1985 |
| JP | H02-057240 B2 | 12/1990 |
| JP | H08-271301 A | 10/1996 |
| JP | H10-104041 A | 4/1998 |
| JP | 2007-303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |
| JP | 2012-105947 A | 6/2012 |
| JP | 2012-225790 A | 11/2012 |
| JP | 2018108356 A | 7/2018 |
| KR | 20070115495 A | 12/2007 |
| NL | 2013740 A | 8/2016 |
| RU | 2615727 C2 * | 4/2017 |
| WO | 1981003427 A1 | 12/1981 |
| WO | 2004045410 A1 | 6/2004 |
| WO | 2013013782 A2 | 1/2013 |
| WO | 20130178742 A1 | 12/2013 |
| WO | 2014/043650 A2 | 3/2014 |
| WO | 2014105755 A1 | 7/2014 |
| WO | 2014108690 A1 | 7/2014 |
| WO | 2014/135856 A1 | 9/2014 |
| WO | 2014/151068 A2 | 9/2014 |
| WO | 2014145971 A2 | 9/2014 |
| WO | 201511402 A1 | 1/2015 |
| WO | 2015/105916 A1 | 7/2015 |
| WO | 2015/127390 A1 | 8/2015 |
| WO | 2015191125 A1 | 12/2015 |
| WO | 2016177901 A1 | 11/2016 |
| WO | 2017/023794 A1 | 2/2017 |
| WO | 2018156624 A1 | 8/2018 |
| WO | 2019066357 A1 | 4/2019 |
| WO | 2019106675 A1 | 6/2019 |

(56) References Cited

FOREIGN PATENT DOCUMENTS

| WO | 2019/226697 A1 | 11/2019 |
|---|---|---|
| WO | 2020033752 A1 | 2/2020 |
| WO | 2020154370 A1 | 7/2020 |
| WO | 2022108589 A1 | 5/2022 |
| WO | 2022182794 A1 | 9/2022 |
| WO | 2023022895 A1 | 2/2023 |
| WO | 2023027871 A1 | 3/2023 |
| WO | 2023076067 A1 | 5/2023 |

OTHER PUBLICATIONS

English translation of Danilov (RU 2615727 C2) (Year: 2017).*
U.S. Appl. No. 15/748,107, filed Jan. 26, 2018 Notice of Allowance dated Dec. 12, 2022.
U.S. Appl. No. 17/054,493, filed Nov. 10, 2020 Non-Final Office Action dated Jan. 27, 2023.
U.S. Appl. No. 17/3026,821, filed May 3, 2021 Non-Final Office Action dated Jan. 10, 2023.
U.S. Appl. No. 17/373,535, filed Jul. 12, 2021 Non-Final Office Action dated Nov. 9, 2022.
Bard Medical, Criticore Disposables—Non I.C., 3 pages, www.bardmedical.com/products/patienl-moniloring-,ystems/criticore®-system/criticore®-disposables-non-ic/ Jan. 30, 2015.
Bard Medical, Criticore Infection Control Disposables, 3 pages, www.bardmedical.com/patienl-monitoring-,ystems/criticore®-system/criticore®-infection-control-disposables/ Jan. 30, 2015.
Bard Medical, Criticore Monitor, 11 pages, www.bardmedical.com/products/patient-monitoring-systems/criticore®-monitor/ Jan. 30, 2015.
Bard Medical, Urine Meiers, 3 pages, www.bardmedical.com/producls/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US2016/044835 filed Jul. 20, 2016 International Search Report and Written Opinion dated Dec. 16, 2016.
U.S. Appl. No. 17/054,493, filed Nov. 10, 2020 Final Office Action dated May 31, 2022.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 17/054,493, filed Nov. 10, 2020 Non-Final Office Action dated Nov. 24, 2021.
PCT/US2022/017574 filed Feb. 23, 2022 Internation Search Report and Written Opinion dated Jun. 8, 2022.
Schlebusch, T. et al., "Bladder volume estimation from electrical impedance tomography" Physiological Measurement Institute of Physics Publishing, Bristol, GB. vol. 35 No. 9 Aug. 20, 2014. (Aug. 20, 2014).
U.S. Appl. No. 17/306,821, filed May 3, 2021 Final Office Action dated Jul. 19, 2023.
U.S. Appl. No. 17/556,907, filed Dec. 20, 2021 Non-Final Office Action dated Aug. 17, 2023.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
DFree Personal—Consumer Product Brochure, 2019.
DFree Pro Brochure 2019.
Leonhäuser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary Volume Monitoring System Based on Bio-Impedance."—Engineering; vol. 5; pp. 321-325; 2013.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
SECA product catalog, https://us.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/373,546, filed Jul. 12, 2021 Non-Final Office Action dated Nov. 1, 2023.
EP 23188337.2 filed May 21, 2019 Extended European Search Report dated Dec. 4, 2023.
PCT/US2019/033389 filed Nov. 26, 2020 Extended European Search Report dated Jun. 4, 2021.
U.S. Appl. No. 17/054,493, filed Nov. 10, 2020 Notice of Allowance dated Jan. 4, 2024.
U.S. Appl. No. 17/556,907, filed Dec. 20, 2021 Notice of Allowance dated Dec. 6, 2023.
PCT/US20/61367 filed Nov. 19, 2020 International Search Report and Written Opinion dated Feb. 22, 2021.
U.S. Appl. No. 17/262,080, filed Jan. 21, 2021 Non-Final Office Action dated Apr. 6, 2023.
U.S. Appl. No. 17/373,535, filed Jul. 12, 2021 Notice of Allowance dated Feb. 23, 2023.
U.S. Appl. No. 17/556,907, filed Dec. 20, 2021 Restriction Requirement dated May 12, 2023.
EP 20962628.2 filed May 31, 2023 Extended European Search Report dated Apr. 20, 2024.
PCT/US2022/039191 filed Aug. 2, 2022 International Search Report and Written Opinion dated Dec. 5, 2022.
PCT/US2022/039746 filed Aug. 8, 2022 International Search Report and Written Opinion dated Nov. 18, 2022.
U.S. Appl. No. 17/306,821, filed May 3, 2021 Notice of Allowance dated Apr. 23, 2024.
U.S. Appl. No. 17/373,546, filed Jul. 12, 2021 Notice of Allowance dated Mar. 7, 2024.
U.S. Appl. No. 17/373,546, filed Jul. 12, 2021 Notice of Allowance dated May 29, 2024.
U.S. Appl. No. 17/552,250, filed Dec. 15, 2021 Non-Final Office Action dated Sep. 19, 2024.
PCT/US2022/046920 filed Oct. 17, 2022 International Search Report and Written Opinion dated Feb. 20, 2023.
U.S. Appl. No. 17/560,079, filed Dec. 22, 2021 Notice of Allowance dated Oct. 29, 2024.
"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/552,250, filed Dec. 15, 2021 Final Office Action dated Feb. 11, 2025.
U.S. Appl. No. 17/587,938, filed Jan. 28, 2022 Restriction Requirement dated Jan. 22, 2025.
U.S. Appl. No. 17/833,682, filed Jun. 6, 2022 Non-Final Office Action dated Jan. 15, 2025.
U.S. Appl. No. 17/870,698, filed Jul. 21, 2022 Restriction Requirement dated Feb. 12, 2025.
U.S. Appl. No. 17/879,658, filed Aug. 2, 2022 Non-Final Office Action dated Dec. 30, 2024.
U.S. Appl. No. 17/893,435, filed Aug. 23, 2022 Non-Final Office Action dated Jan. 17, 2025.
U.S. Appl. No. 17/552,250, filed Dec. 15, 2021 Advisory Action dated May 8, 2025.
U.S. Appl. No. 17/552,250, filed Dec. 15, 2021 Notice of Allowance dated May 20, 2025.

(56) References Cited

OTHER PUBLICATIONS

U.S. Appl. No. 17/587,938, filed Jan. 28, 2022 Non-Final Office Action dated May 12, 2025.
U.S. Appl. No. 17/682,785, filed Feb. 28, 2022 Restriction Requirement dated Apr. 2, 2025.
U.S. Appl. No. 17/833,682, filed Jun. 6, 2022 Final Office Action dated May 12, 2025.
U.S. Appl. No. 17/863,223, filed Jul. 12, 2022 Non-Final Office Action dated Apr. 2, 2025.
U.S. Appl. No. 17/863,923, filed Jul. 13, 2022 Restriction Requirement dated May 21, 2025.
U.S. Appl. No. 17/870,698, filed Jul. 21, 2022 Non-Final Office Action dated Apr. 9, 2025.
U.S. Appl. No. 17/873,834, filed Jul. 26, 2022 Non-Final Office Action dated May 19, 2025.
U.S. Appl. No. 17/879,658, filed Aug. 2, 2022 Final Office Action dated May 14, 2025.
U.S. Appl. No. 17/883,507, filed Aug. 8, 2022 Restriction Requirement dated May 19, 2025.
U.S. Appl. No. 18/278,167 filed Aug. 21, 2023 Non-Final Office Action dated Apr. 24, 2025.

\* cited by examiner

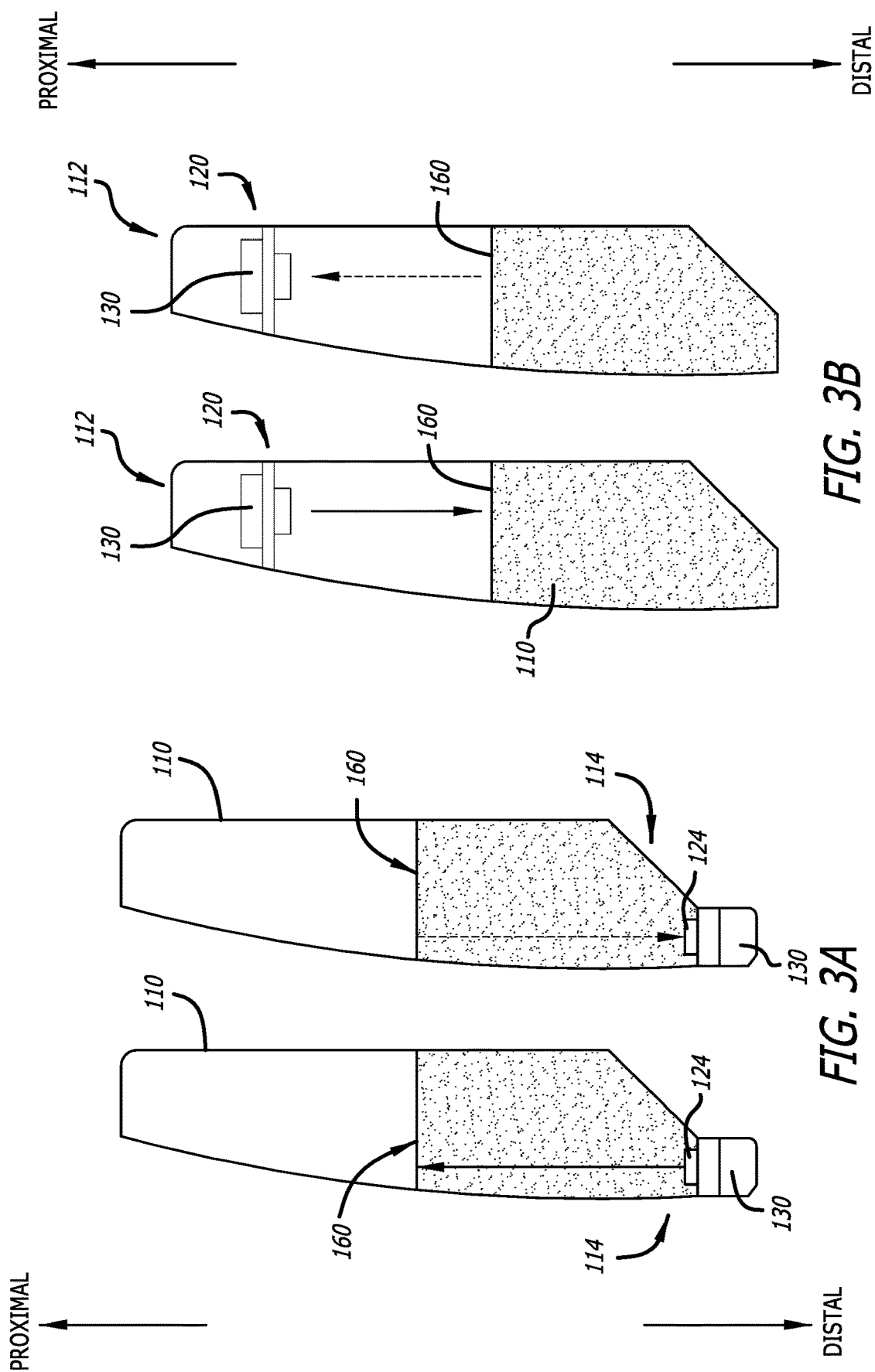

AUTOMATED URINARY OUTPUT-MEASURING SYSTEMS AND METHODS

PRIORITY

This application claims the benefit of priority to U.S. Provisional Patent Application No. 63/128,558, filed Dec. 21, 2020, which is incorporated by reference in its entirety into this application.

BACKGROUND

Low urinary output in those with congestive heart failure ("CHF") can be a symptom of low cardiac output. It can be difficult to non-invasively measure urinary output in those with CHF as they are often ambulatory, and most automated urinary output measuring devices are invasive and engineered for the intensive care unit and non-ambulatory patients. It would be beneficial to CHF patients and clinicians to be able to measure urinary output accurately and automatically in ambulatory CHF patients.

Disclosed herein are automated urinary output ("UO")-measuring systems and methods that address the foregoing.

SUMMARY

Disclosed herein is an automated UO-measuring system including a container configured to collect fluid, the container having a console, one or more ultrasonic sensors coupled to the console, one or more accelerometers coupled to the console, and a valve configured to pass fluid therethrough. The system also includes a fluid line coupled to the valve and a container holder. The container holder has a sleeve configured to be secured to a user and a pocket configured to securely hold the container.

In some embodiments, the console, the one-or-more ultrasonic sensors, the one-or-more accelerometers, and the valve are organized into a panel.

In some embodiments, the panel divides the container into a proximal section or a distal section.

In some embodiments, the panel is located at a proximal end or a distal end of the container.

In some embodiments, the panel includes a pump configured to create a low-pressure environment inside the container.

In some embodiments, the console includes one of more processors, a non-transitory storage medium, an energy source and one or more logic modules.

In some embodiments, the one-or-more logic modules are configured to receive accelerometer values from the one-or-more accelerometers, determine an acceleration state of the container, activate the one-or-more ultrasonic sensors, receive ultrasonic sensor values from the one-or-more ultrasonic sensors, correlate the ultrasonic sensor values with a volume-of-voided-urine value within the container and a time-of-day value for a correlation, determine a volume of urine using the ultrasonic sensor values, activate a pump to create and maintain a low-pressure environment inside the container, transmit the correlation to a computing device, or a combination thereof.

In some embodiments, the one-or-more logic modules are configured to activate the one-or-more ultrasonic sensors occurs when the acceleration state of the container is below a threshold.

In some embodiments, the container holder is configured to be detachably secured to the user.

In some embodiments, the sleeve includes two or more arms configured to wrap around an appendage of the user.

In some embodiments, the two-or-more arms are organized into a first pair of fastening arms and a first pair of securing arms.

In some embodiments, the container holder is secured to the appendage of the user by hook-and-loop fasteners or magnets.

In some embodiments, the sleeve includes a compression sock configured to be slidably secured to an appendage of the user.

In some embodiments, the container includes a rigid container.

Also disclosed herein is a method of automatically measuring urine output including capturing a volume of voided urine from a user, in a container using a fluid line, the container being coupled to the user, distal a bladder of the user, the container having a valve configured to pass fluid therethrough and a console coupled to one or more ultrasonic sensors and one or more accelerometers. The method also includes detecting an acceleration state of the container, measuring the volume of voided urine over time in the container, correlating the measured volume of voided urine with a volume value and a time-of-day value, and transmitting the volume value and the time-of-day value to a computing device.

In some embodiments, capturing the volume of voided urine from the user includes maintaining a low-pressure environment in the container with a pump of the container.

In some embodiments, detecting the acceleration state of the container includes using the one-or-more accelerometers to detect the acceleration state of the container.

In some embodiments, measuring the volume of voided urine over time in the container includes measuring the volume when the acceleration state of the container is zero.

In some embodiments, measuring the volume of voided urine over time in the container includes using the one-or-more ultrasonic sensors to measure the volume of voided urine over time.

In some embodiments, measuring the volume of voided urine over time in the container includes both measuring and recording at evenly spaced time intervals.

In some embodiments, the time intervals are user-defined.

In some embodiments, transmitting the volume value and the time-of-day value to the computing device includes wirelessly transmitting the volume value and the time-of-day value to the computing device.

These and other features of the concepts provided herein will become more apparent to those of skill in the art in view of the accompanying drawings and following description, which describe particular embodiments of such concepts in greater detail.

DRAWINGS

A more particular description of the automated UO-measuring systems and methods will be rendered by reference to specific embodiments thereof that are illustrated in the drawings. It is appreciated that these drawings depict only some embodiments of the foregoing and are, therefore, not to be considered limiting to the scope of the concepts provided herein. Example embodiments will be described and explained with additional specificity and detail through the use of the accompanying drawings in which:

FIG. 3A illustrates a method of measuring urinary output in accordance with some embodiments FIG. 3B illustrates another method of measuring urinary output in accordance with some embodiments.

DESCRIPTION

Figure 1B:
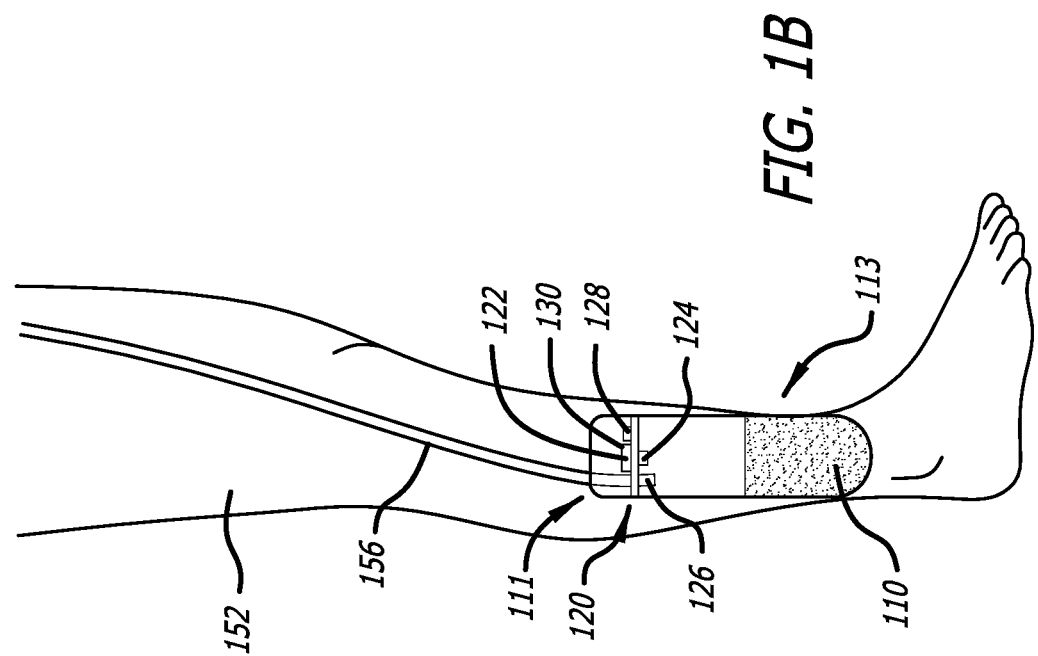
FIG. 1B illustrates a perspective view of the automated UO-measuring system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a container disclosed herein includes a portion of the container intended to be near a clinician when the container is used on a user. Likewise, a "proximal length" of, for example, the container includes a length of the container intended to be near the clinician when the container is used on the user. A "proximal end" of, for example, the container includes an end of the container intended to be near the clinician when the container is used on the user. The proximal portion, the proximal-end portion, or the proximal length of the container can include the proximal end of the container; however, the proximal portion, the proximal-end portion, or the proximal length of the container need not include the proximal end of the container. That is, unless context suggests otherwise, the proximal portion, the proximal-end portion, or the proximal length of the container is not a terminal portion or terminal length of the container.

With respect to "distal," a "distal portion" or a "distal-end portion" of, for example, a container disclosed herein includes a portion of the container intended to be near or in a user when the container is used on the user. Likewise, a "distal length" of, for example, the container includes a length of the container intended to be near or in the user when the container is used on the user. A "distal end" of, for example, the container includes an end of the container intended to be near or in the user when the container is used on the user. The distal portion, the distal-end portion, or the distal length of the container can include the distal end of the container; however, the distal portion, the distal-end portion, or the distal length of the container need not include the distal end of the container. That is, unless context suggests otherwise, the distal portion, the distal-end portion, or the distal length of the container is not a terminal portion or terminal length of the container.

Alternatively, logic can be software, such as executable code in the form of an executable application, an Application Programming Interface (API), a subroutine, a function, a procedure, an applet, a servlet, a routine, source code, object code, a shared library/dynamic load library, or one or more instructions. The software can be stored in any type of a suitable non-transitory storage medium, or transitory storage medium (e.g., electrical, optical, acoustical or other form of propagated signals such as carrier waves, infrared signals, or digital signals). Examples of non-transitory storage medium can include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code can be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN," etc.), or a combination of networks. Examples of a computing device can include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message can be in the form of one or more packets, frames, HTTP-based transmissions, or any other series of bits having the prescribed format.

Unless defined otherwise, all technical and scientific terms used herein have the same meaning as commonly understood by those of ordinary skill in the art.

Figure 1A:
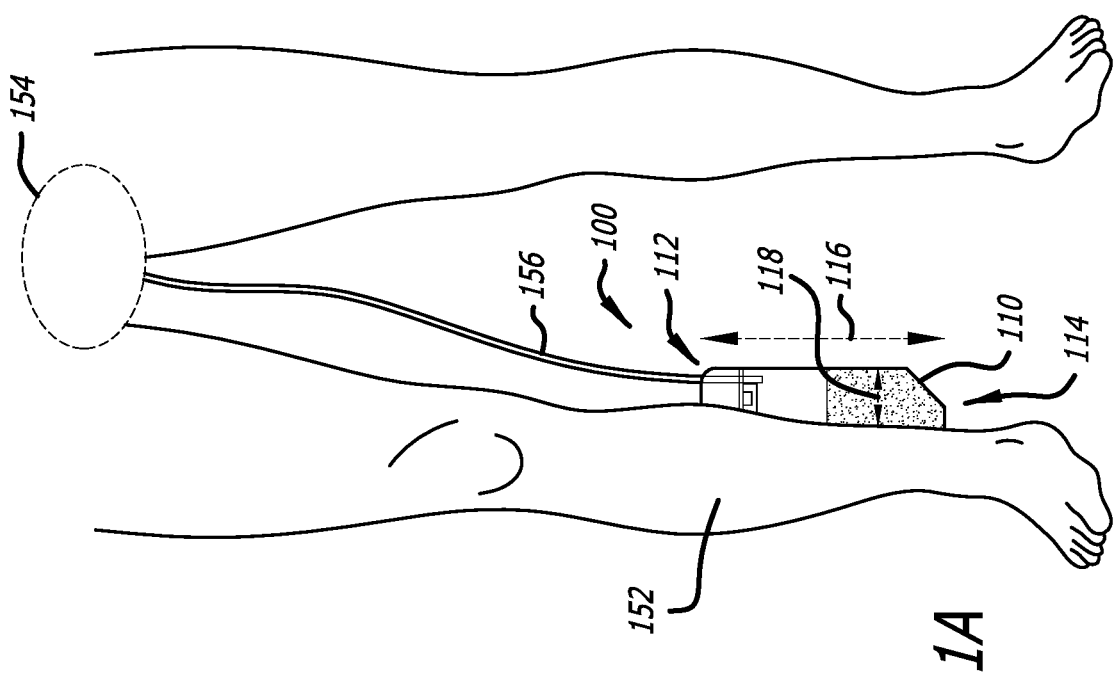
FIG. 1A illustrates a perspective view of an automated UO-measuring system in accordance with some embodiments.

FIG. 1A illustrates a perspective view of an automated UO-measuring system 100 in accordance with some embodiments. In some embodiments, the automated UO-measuring system 100 includes a container 110 configured to receive and contain a volume of voided urine generated by a user or patient. In some embodiments, the container 110 can be a rigid container, which includes a container length 116, a container depth 118 and is configured to contain a volume of fluid therein. As used herein, a rigid container means a container that is stiff and unyielding as opposed to pliant or flexible. In some embodiments, the container 110 is clear, for visual determination of the fluid volume therein. The container 110 can be configured to have various shapes including a triangular prism, a rectangular prism, a pentagonal prism, an irregular prism, a cylinder, a polyhedron or the like. In some embodiments, the container 110 has a fixed three-dimensional structure. In an embodiment, the container 110 includes a cavity configured to fit the container 110 flush against a user's appendage 152. In some embodiments, the container 110 can be constructed of a hardened polymer such polycarbonate, polyethylene, polypropylene, polystyrene or the like.

In some embodiments, the container 110 includes a valve 126 on a proximal end 112 of the container 110. In some embodiments, the valve 126 can include a directional valve, a check valve, umbrella valve, flapper valve or the like. In some embodiments, the valve 126 can be configured to be removed, to dispose of the volume of voided urine in the container 110. In some embodiments, a fluid line 156 from the user configured to transport voided urine therein, can be distally coupled to the valve 126 of the container 110. In some embodiments, the fluid line 156 can include a hollow tubing constructing of a clear plastic polymer such as polycarbonate, polyethylene terephthalate, polystyrene, urethane, nylon or the like. In some embodiments, the fluid line 156 can be coupled to a urine collection device, wherein the urine collection device is configured to capture a volume of voided urine from the user's bladder 154 and the fluid line 156 is configured to channel the urine to the container 110 through the valve 126. The container 110 is configured to be secured to a user, distal of the user's bladder 154 in order to allow fluid flow to the container 110 through passive gravity flow. For example, in some embodiments, the container 110 can be secured to a thigh, a calf or an ankle.

FIG. 1B illustrates a perspective view of the automated UO-measuring system 100 in accordance with some embodiments. In some embodiments, the container 110 includes the valve 126, one or more accelerometers 122, one or more ultrasonic sensors 124 and a console 130. In some embodiments, the valve 126, the one-or-more accelerometers 122, the one-or-more ultrasonic sensors 124 and the console 130 can be organized into a panel 120. In some embodiments, the panel 120 can be proximally located or distally located on the container 110. The one-or-more accelerometers 122 can be configured to detect when the container 110 is accelerating or not such that the fluid level within the container 110 can be determined when the container 110 is not accelerating. The one-or-more ultrasonic sensors 124 can be configured to detect the fluid level within the container 110 that will be described in more detail herein. The console 130 can be configured to receive accelerometer values from the one-or-more accelerometers 122, receive detected ultrasonic measurements from the one-or-more ultrasonic sensors 124 and transmit the measured or determined values in a message to a computing device that will be described in more detail herein. In some embodiments, the computing device can include a computing device, a smartphone, a medical device, a laptop or the like.

In some embodiments, the panel 120 can be configured to divide the container 110 into a proximal section 111 and a distal section 113. The container 110 can be configured to detachably separate at the panel 120, into the proximal section 111 and the distal section 113, and can be configured to be rejoined into one piece through a press fit, a snap fit, an interference fit or the like. In some embodiments, the container 110 can be configured to detachably separate to dispose of the volume of voided urine. In some embodiments, the panel 120 can be secured within the proximal section 111. In some embodiments, the fluid line 156 can be detached from the valve 126 to dispose of the volume of voided urine through the valve 126.

Figure 1C:
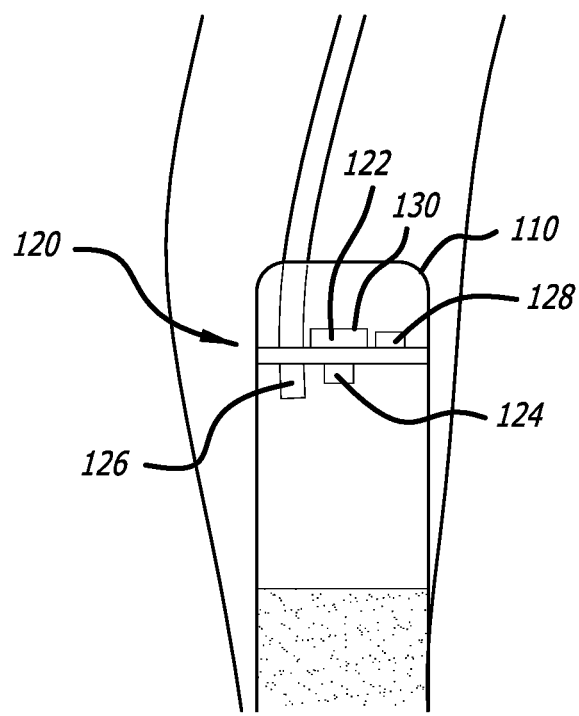
FIG. 1C illustrates a side view of a container of the automated UO-measuring system in accordance with some embodiments.

FIG. 1C illustrates a side view of the container 110 including the panel 120 of the automated UO-measuring system 100 in accordance with some embodiments. In some embodiments, the panel 120 includes a pump 128 configured to evacuate air from the container 110 to create a low-pressure environment inside the container 110 to assist urine drainage into the container 110. In some embodiments, the pump 128 is coupled to the console 130 and controlled by the console 130. In some embodiments, the pump 128 can be configured to be activated after the volume of voided urine within the container 110 has be disposed. In some embodiments, the pump 128 includes a pressure sensor configured to detect the pressure within the container 110 in order to maintain a consistent low-pressure environment in the container 110.

Figure 2:
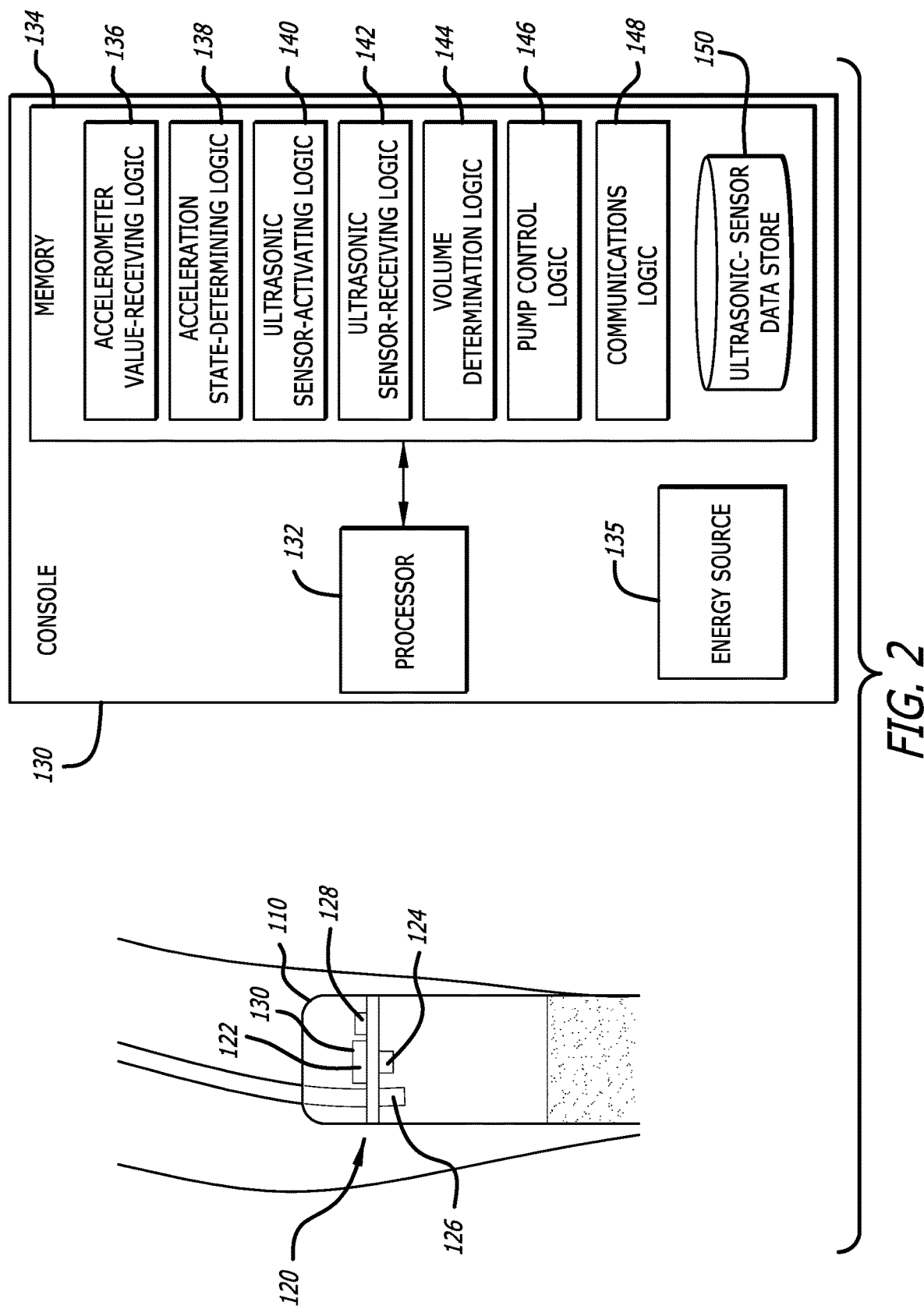
FIG. 2 illustrates a block diagram of some components of the automated UO-measuring system in accordance with some embodiments.

FIG. 2 illustrates a block diagram of some components of the automated UO-measuring system 100 in accordance with some embodiments. In some embodiments, the automated UO-measuring system 100 includes the console 130. In some embodiments, the console 130 can be contained within the panel 120 or coupled separately to the container 110. The console 130 includes one or more processors 132, non-transitory storage medium ("memory") 134, an energy source 135 and one or more logic modules such as a plurality of logic modules. In some embodiments, the energy source 135 can be configured to provide energy to the one-or-more accelerometers 122, the one-or-more ultrasonic sensors 124, the pump 128, and the console 130. In some embodiments, the console 130 can be configured to detect data and transmit the detected data to a computing device for processing. In some embodiments, the one-or-more logic modules are selected from an accelerometer value-receiving logic 136, an acceleration state-determining logic 138, an ultrasonic sensor-activating logic 140, an ultrasonic sensor-receiving logic 142, a volume determination logic 144, a pump control logic 146, and a communications logic 148. In some embodiments, the memory 134 can include a data store such as an ultrasonic-sensor data store 150. The accelerometer value-receiving logic 136 can be configured to receive measured accelerometer values from the one-or-more accelerometers 122. In some embodiments, the acceleration state-determining logic 138 can be configured to determine an acceleration state of the container 110 based on the measured accelerometer values. In some embodiments, the acceleration state-determining logic 138 can determine the acceleration state of the container 110 by determining if the accelerometer values are above or below a near-zero threshold accelerometer value. In some embodiments, the ultrasonic sensor-activating logic 140 can be configured to activate the one-or-more ultrasonic sensors 124. In some embodiments, the ultrasonic sensor-activating logic 140 can be configured to activate the one-or-more ultrasonic sensors 124 only when the console 130 determines the container 110 has an acceleration state that is about zero, for example, by way of comparison to the near-zero threshold accelerometer value. In some embodiments, the ultrasonic sensor-receiving logic 142 can be configured to receive a measured time value of the time it takes an ultrasonic wave generated by the one-or-more ultrasonic sensors 124 to be detected after reflection inside the container 110, that will be described in more detail herein.

In some embodiments, the volume determination logic 144 can be configured to determine the volume of voided urine contained within the container 110 by correlating the measured time value of the reflected ultrasonic wave with a volume value corresponding to the volume of voided urine within the container 110. In some embodiments, the volume determination logic 144 can be further configured to associate a time-of-day value with each the volume value at the time of day the volume value was determined. In some embodiments, the volume determination logic 144 can be configured to generate an associated pairing of the {time-of-day value, volume value}. In some embodiments, the volume determination logic 144 can be configured to associate other parameters with the associated pairing in an associated trio, an associated quartet, an associated quintet, and an associated sextet or the like. For example, the volume determination logic 144 can associate a device-operating-condition value, a voided number in a user-defined timer-period value, a device-status value or the like. In some embodiments, the pump control logic 146 can be configured to activate the pump 128 to create the low-pressure environment within the container 110. In some embodiments, the pump control logic 146 can be configured to activate the pump 128 to maintain the low-pressure environment within the container 110. In an embodiment, the pump 128 includes the pressure sensor configured to detect the pressure within the container 110 and acquire pressure readings within the container 110. In this embodiment, the pressure sensor can transmit the pressure readings to the console 130 and the pump control logic 146 can be configured to activate the pump 128 to maintain a consistent low-pressure environment within the container 110. In some embodiments, a low-pressure environment within the container 110 can be configured to help draw fluid into the container 110.

The ultrasonic-sensor data store 150 can be configured to store the volume values, the measured time values from the one-or-more ultrasonic sensors 124, the time-of-day values, the device-status value, the device-operating-condition value, the voided number in the user-defined time-period value or a combination thereof. In some embodiments, the ultrasonic-sensor data store 150 can store the volume values and time-of-day values as the associated pairings of {time-of-day value, volume value}. In some embodiments, the communications logic 148 can be configured to transmit each associated pairing of {time-of-day value, volume value} to a computing device, an electronic medical record ("EMR") system or the like. The communications logic 148 can be configured to wirelessly transmit the associated pairings of {time-of-day value, volume value} to the computing device. Wireless communication modalities can include Wi-Fi, Bluetooth®, Near Field Communications (NFC), cellular Global System for Mobile Communication ("GSM"), electromagnetic (EM), radio frequency (RF), combinations thereof, or the like.

In some embodiments, the one-or-more accelerometers 122 can be configured to detect acceleration of the container 110 at regular timed intervals (e.g., every five minutes, every hour, every 30 seconds, or the like). In some embodiments, the one-or-more accelerometers 122 can be configured to detect acceleration of the container 110 at user-defined intervals. The automated UO-measuring system 100 can be configured to take a volume value every time the accelerometer value is below the near-zero threshold accelerometer value. In some embodiments, the automated UO-measuring system 100 can be configured to take a volume value when two consecutive accelerometer values are below the near-zero threshold accelerometer value. In some embodiments, the automated UO-measuring system 100 can be configured to take a volume value at either regular timed intervals or the user-defined intervals. In an embodiment, the user can define how many volume values the console 130 generates in a specific time period. For example, the user can desire 8 volume values in 8 hours and the automated UO-measuring system 100 can be configured to detect 1 volume value per hour or the automated UO-measuring system 100 can be configured to continually detect the acceleration state of the container 110 until 1 volume value is obtained within the hour time block.

In an embodiment, the one-or-more accelerometers 122 can be configured to detect accelerometer values of the container 110 at a regular timed interval of once every one hour. In this embodiment, if the one-or-more accelerometers 122 do detect accelerometer values of the container 110 greater than the near-zero threshold accelerometer value during the hour, the one-or-more accelerometers 122 can be configured to either wait until the next hour to detect accelerometer values of the container 110 or can wait a certain amount of time (e.g. 5 minutes) to commence detecting accelerometer values of the container 110.

In some embodiments, the console 130 can be configured to notify the user when the volume value of the volume of voided urine within the container 110 is approaching the maximum allowable volume within the container 110. In some embodiments, the maximum allowable volume can be the maximum allowable volume contained within the container 110 or can be the maximum volume of voided urine the container 110 can hold before the volume of voided urine expands into the proximal section 111 of the container 110. The console 130 can wirelessly send the information to the computing device to notify the user through visual or an audible signal.

FIGS. 3A-3B illustrate methods of measuring urinary output in accordance with some embodiments. In some embodiments, as illustrated in FIG. 3A, the panel 120 including the one-or-more accelerometers 122, the one-or-more ultrasonic sensors 124 and the console 130 can be located at a distal end 114 of the container 110. The panel 120 arranges the one-or-more ultrasonic sensors 124 to be pointing proximally, towards an air/urine interface 160. The one-or-more accelerometers 122 can detect accelerometer values of the container 110 that can then be used by the console 130 to determine the acceleration state of the container 110. In some embodiments, the console 130 can be configured to activate the one-or-more ultrasonic sensors 124 only when the acceleration of the container 110 is below the near-zero threshold accelerometer value. Once the acceleration of the container 110 is below the near-zero threshold accelerometer value, the one-or-more ultrasonic sensors 124 can generate an ultrasonic wave that travels proximally through the urine until the ultrasonic wave reaches the urine/air interface 160. The ultrasonic wave is then reflected distally back through the urine, until the ultrasonic wave reaches the one-or-more ultrasonic sensors 124. The time from generation of the ultrasonic wave to the time a sensor of the one-or-more ultrasonic sensors 124 receives the reflection can be measured and transmitted to the console 130. The console 130 can be configured to send the information to the computing device to correlate the measured time to a volume value that correlates to the volume of voided urine within the container 110. In some embodiments, the console 130 can be configured to send the information to the computing device to correlate the volume value with a time-of-day value, which can be transmitted to a computing device.

As illustrated in FIG. 3B, in some embodiments, the panel 120 can be located at the proximal end 112 of the container 110. The panel 120 arranges the one-or-more ultrasonic sensors 124 to be pointing distally, towards the air/urine interface 160. Once the acceleration of the container 110 is below the near-zero threshold accelerometer value, the console 130 can be configured to activate the one-or-more ultrasonic sensors 124. The one-or-more ultrasonic sensors 124 can generate an ultrasonic wave that travels distally through the air until the ultrasonic wave reaches the air/urine interface 160. The ultrasonic wave is then reflected proximally back through the air, until the ultrasonic wave reaches the one-or-more ultrasonic sensors 124. The time from generation of the ultrasonic wave to the one-or-more ultrasonic sensors 124 receiving the reflection of the ultrasonic wave can be measured and transmitted to the console 130. The console 130 can be configured to correlate the measured time to a volume value of the volume of voided urine in the container 110. The console 130 can also be configured to correlate the volume value with a time-of-day value, which can be transmitted to a computing device.

In an embodiment, the valve 126 can be located at the proximal end 112 of the container 110 and the panel 120 including the one-or-more accelerometers 122 and the one-or-more ultrasonic sensors 124 can be located at the distal end 114 of the container 110. The one-or-more ultrasonic sensors 124 can generate an ultrasonic wave that travels through the volume of voided urine until the wave reaches the urine/air interface 160 where it is reflected back to the one-or-more ultrasonic sensors 124.

Figure 4B:
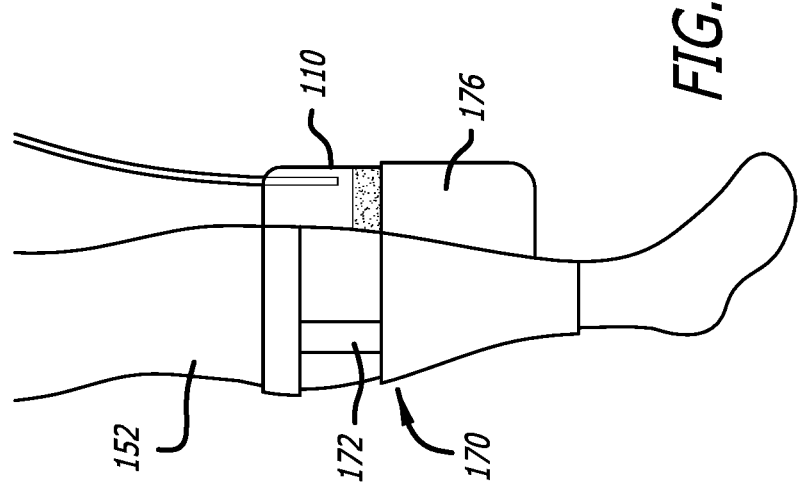
FIG. 4B illustrates the container holder of FIG. 4A in use in accordance with some embodiments.
Figure 4A:
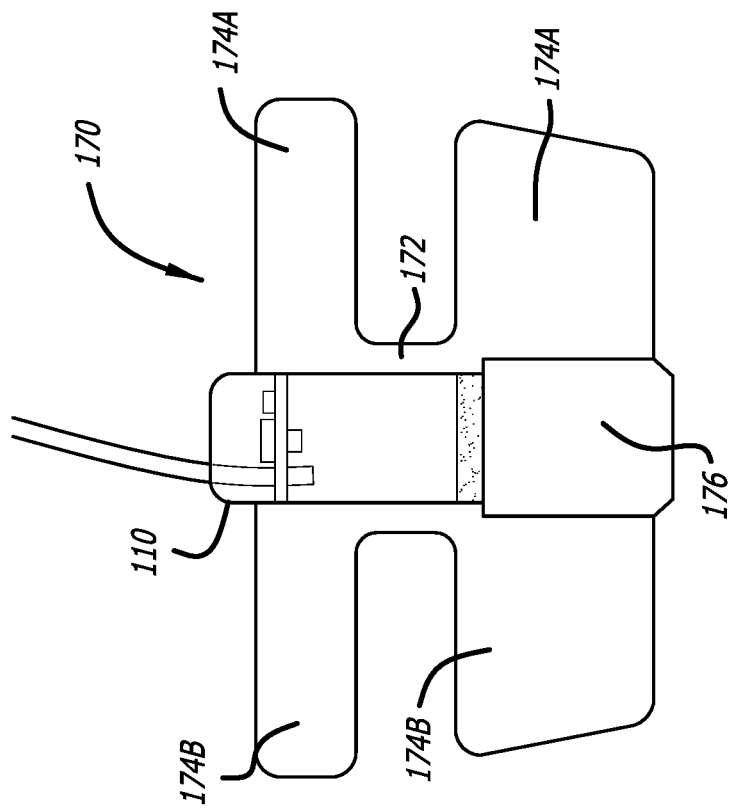
FIG. 4A illustrates a container holder of the automated UO-measuring system in a ready-to-use state in accordance with some embodiments.

FIGS. 4A-4B illustrate a container holder ("holder") 170 of the automated UO-measuring system 100 in accordance with some embodiments. In some embodiments, the container 110 can be secured to the user's appendage 152 by the holder 170. In some embodiments, the holder 170 can include a sleeve 172 having a pocket 176 configured to securely hold the container 110 therein. As used herein, "securely held" means held so that the container 110 is firmly positioned so as not to become easily displaced to prevent user discomfort. In some embodiments, the sleeve 172 can be constructed of one or more fabrics configured to provide a compressing force on the user's appendage 152 to prevent unwanted movement of the holder 170. In some embodiments, the pocket 176 can be constructed of one or more fabrics configured to provide a compressing force on the container 110 to prevent unwanted movement of the container 110. In some embodiments, the holder 170 can include two or more arms such as the first pair of fastening arms 174A and the first pair of securing arms 174B extending laterally from the sleeve 172. Indeed, as illustrated in FIG. 4A, the holder 170 can include a first pair of fastening arms 174A and a first pair of securing arms 174B. In some embodiments, as illustrated in FIG. 4B, the first pair of fastening arms 174A can be configured to wrap around the user's appendage 152 and be detachably secured to the first pair of securing arms 174B. In some embodiments, the first pair of fastening arms 174A can be detachably coupled to the first pair of securing arms 174B by hook-and-loop fasteners, magnets or the like. In some embodiments, the first pair of fastening arms 174A can include the hook components of the hook-and-loop fasteners and the first pair of securing arms 174B can include the loop components of the hook-and-loop fasteners. In some embodiments, the first pair of fastening arms 174A can include the loop components of the hook-and-loop fasteners and the first pair of securing arms 174B can include the hook components of the hook-and-loop fasteners.

Figure 5B:
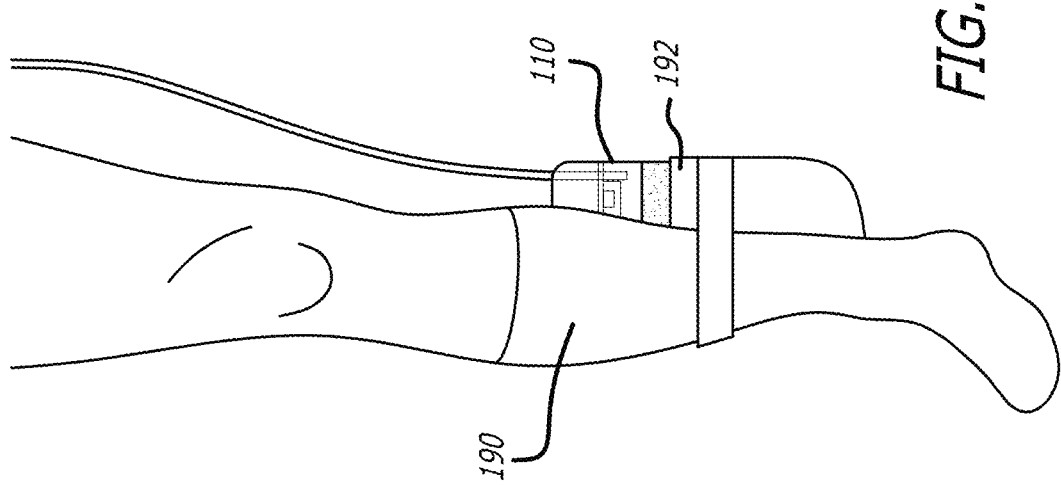
FIG. 5B illustrates a front view of the container holder of FIG. 5A in use in accordance with some embodiments.
Figure 5A:
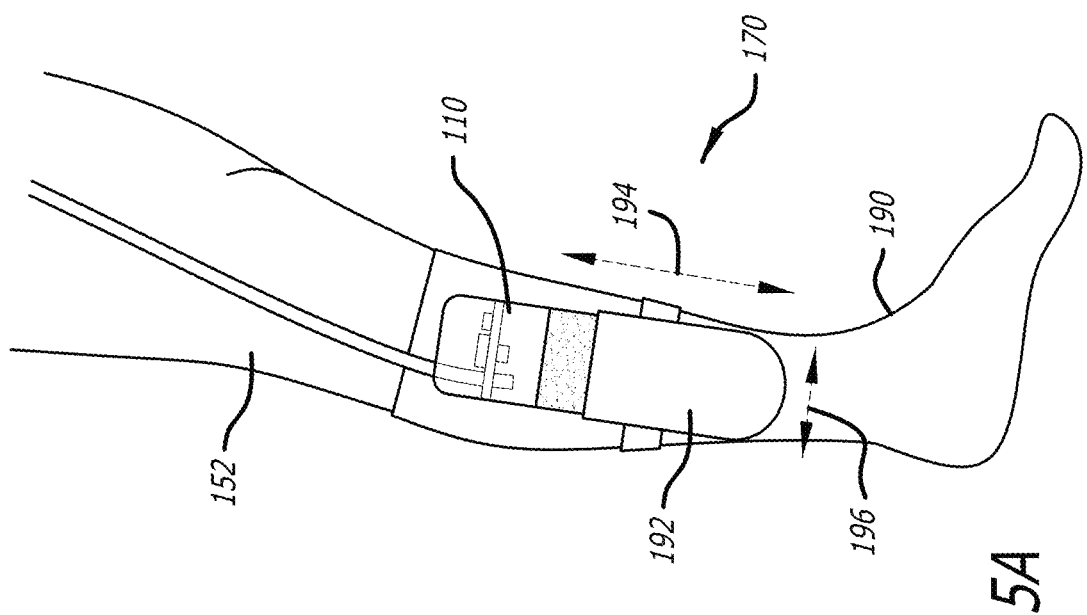
FIG. 5A illustrates a side view of another container holder of the automated UO-measuring system in use in accordance with some embodiments.

FIGS. 5A-5B illustrate different views of the holder 170 of the automated UO-measuring system 100 in accordance with some other embodiments. In some embodiments, as illustrated in FIG. 5A, the user can couple the container 110 to his or her appendage 152 by using a compression sock 190 having a pouch 192. In some embodiments, the pouch 192 can be configured to slidably receive the container 110 therein. The compression sock 190 can be configured to have the pouch 192 located medially or more offset from a midline. The compression sock 190 and the pouch 192 can be constructed from one or more fabrics that are configured to provide a compressing force on the container 110 to prevent unwanted movement of the container 110. In some embodiments, the pouch 192 has a pouch length 194 and pouch width 196. In some embodiments, the pouch length 194 can be smaller than the container 110, equal to the container 110 or greater than the container 110. Although FIGS. 4A-4B and FIGS. 5A-5B illustrate various embodiments of the holder 170 of the automated UO-measuring system 100, it can be appreciated that other methods of coupling the container 110 to the user's appendage 152 are considered.

Figure 6:
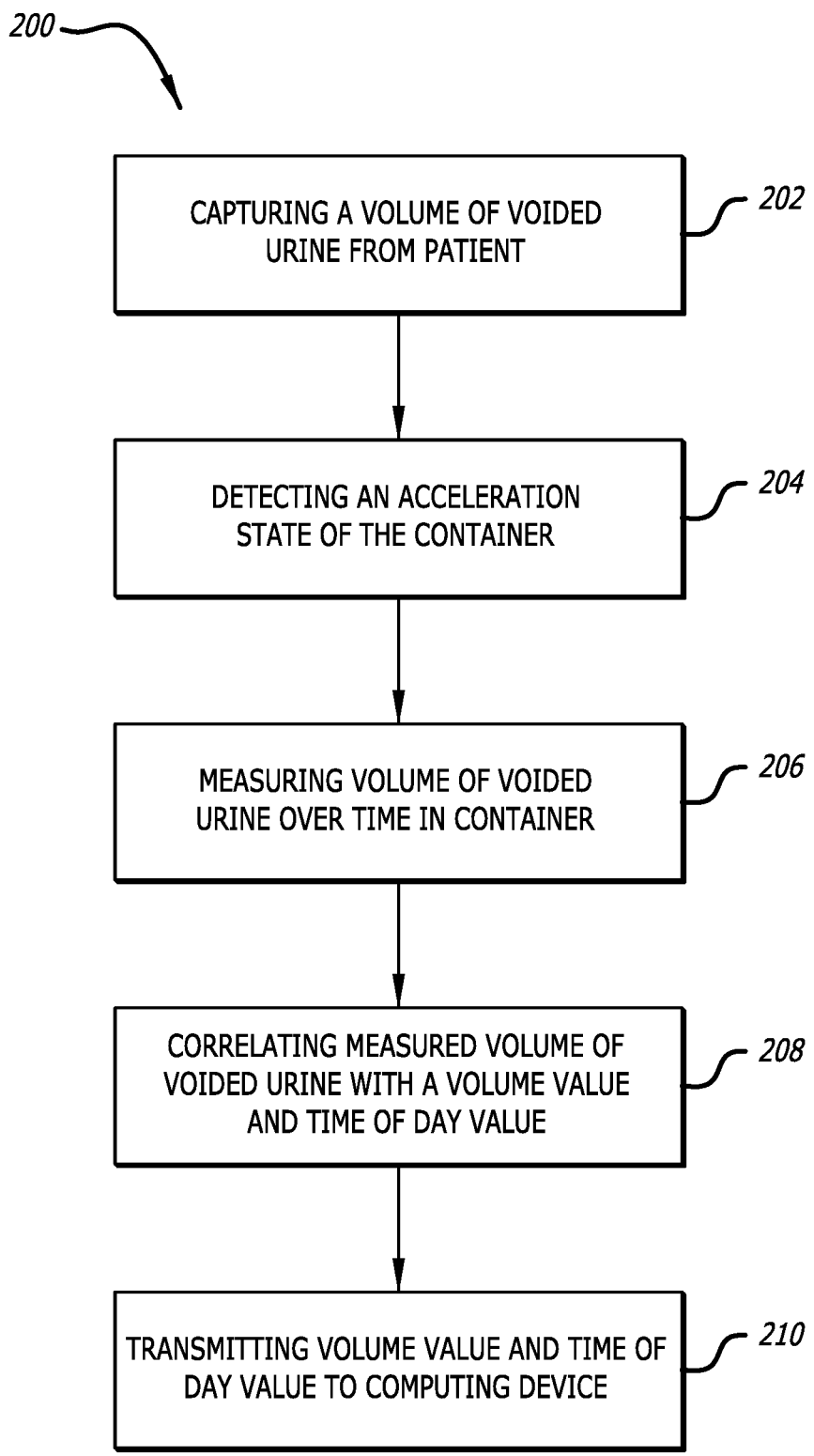
FIG. 6 illustrates a flow chart of a method of measuring urinary output using the automated UO-measuring system in accordance with some embodiments.

FIG. 6 illustrates a flow chart of a method 200 of automatically measuring urinary output using the automated UO-measuring system 100 in accordance with some embodiments. In some embodiments, the method 200 includes capturing voided urine from a user (block 202). In some embodiments, capturing voided urine includes using the automated UO-measuring system 100 including the container 110 configured to collect fluid therein, the container 110 having the console 130 coupled to the one-or-more accelerometers 122 and the one-or-more ultrasonic sensors 124, and having the valve 126 configured to pass fluid therethrough. In some embodiments, the container 110 is a rigid container. The automated UO-measuring system 100 further includes a fluid line 156 coupled to the valve 126. The automated UO-measuring system 100 further includes the holder 170 having the sleeve 172 configured to be coupled or secured to the user or the user's appendage 152, distal of the user's bladder 154, the sleeve 172 having the pocket 176 configured to securely hold the container 110 therein. In some embodiments, securing the container 110 with the container holder 170, distal of the user's bladder 154 allows for fluid flow into the container 110 through passive gravity flow. In some embodiments, capturing voided urine includes using a urine collection device coupled to the fluid line 156 configured to channel urine from the user's bladder 154 to the container 110. In some embodiments, capturing a volume of voided urine includes the container 110 having the pump 128 configured to maintain a low-pressure environment in the container 110. In some embodiments, maintaining a low-pressure environment within the container 110 contributes to passive fluid flow into the container 110.

In some embodiments, the method 200 includes detecting an acceleration state of the container 110 (block 204). In some embodiments, detecting the acceleration of the container 110 includes using the one-or-more accelerometers 122 to obtain accelerometer values of the container 110. In some embodiments, the accelerometer values are transmitted to the console 130 and to the computing device where the acceleration state of the container 110 can be determined by comparing the accelerometer values with the near-zero threshold accelerometer value. In some embodiments, detecting the acceleration state of the container 110 includes detecting accelerometer values at regular time intervals, user-defined intervals or continuously detecting accelerometer values.

In some embodiments, the method 200 further includes measuring the volume of voided urine over time in the container 110 (block 206). In some embodiments, measuring the volume of voided urine over time includes measuring the volume of voided urine when the acceleration state of the container 110 is below the near-zero threshold accelerometer value. In some embodiments, measuring the volume of voided urine over time in the container 110 includes generating one or more ultrasonic waves by the one-or-more ultrasonic sensors 124 that travel through the air in the container 110 until the ultrasonic waves reach the air/urine interface 160. Once reaching the air/water interface 160, the ultrasonic waves are reflected back towards the one-or-more ultrasonic sensors 124. In some embodiments, the one-or-more ultrasonic sensors 124 can generate one or more ultrasonic waves that travel through the urine in the container 110 until the ultrasonic waves reach the urine/air interface 160 where they are reflected back through the urine to the one-or-more ultrasonic sensors 124. The time from generation of the ultrasonic wave to receiving the reflected ultrasonic wave can be measured and transmitted to the console 130.

In some embodiments, the method 200 includes correlating the measured volume of voided urine with a volume value and a time-of-day value (block 208). In some embodiments, correlating the measured volume of voided urine with a volume value includes the console 130 correlating the measured time with the volume value, corresponding to the volume of voided urine within the container 110. In some embodiments, correlating the measured volume of voided urine with a volume value and a time-of-day value includes the console 130 and the computing device correlating the volume value with the time-of-day value. In some embodiments, correlating the measured volume of voided urine with a volume value and a time-of-day value includes generating an associated pairing of {time-of-day value, volume value}. In some embodiments, measuring the volume of voided urine over time includes measuring the volume of voided urine at automatically defined or user-defined time intervals.

In some embodiments, the method 200 includes transmitting the volume value and time-of-day value to a computing device (block 210). In some embodiments, transmitting the volume value and time-of-day value to the computing device includes transmitting the associated pairings of {time-of-day value, volume value}. In some embodiments, transmitting the volume value and time-of-day value to the computing device includes transmitting an associated trio of {device-operating-condition value, time-of-day value, volume value}. In some embodiments, transmitting the volume value and time-of-day value to the computing device includes wirelessly transmitting from the console 130 to the computing device. Wireless communication modalities can include Wi-Fi, Bluetooth®, Near Field Communications (NFC), cellular Global System for Mobile Communication ("GSM"), electromagnetic (EM), radio frequency (RF), combinations thereof, or the like. In some embodiments, transmitting the volume value and time-of-day value to the computing device includes transmitting the volume value and time-of-day value as each is measured or determined. In some embodiments, transmitting the volume value and time-of-day value to a computing device includes transmitting the associated volume value and time-of-day value pairing at the end of a user-defined time interval. In some embodiments, transmitting the associated volume value and time-of-day value pairing at includes transmitting the associated trio of {device-operating-condition value, time-of-day value, volume value} at the end of the user-defined time interval. In some embodiments, transmitting the volume value and the time-of-day value to the computing device includes transmitting the volume value and time-of-day value before the volume of voided urine is disposed out of the container 110.

While some particular embodiments have been disclosed herein, and while the particular embodiments have been disclosed in some detail, it is not the intention for the particular embodiments to limit the scope of the concepts provided herein. Additional adaptations and/or modifications might appear to those of ordinary skill in the art, and, in broader aspects, these adaptations and/or modifications are encompassed as well. Accordingly, departures can be made from the particular embodiments disclosed herein without departing from the scope of the concepts provided herein.

What is claimed is:

1. An automated urinary output ("UO")-measuring system, comprising:
 a container configured to collect fluid therein, the container comprising:
  a console;
  one or more ultrasonic sensors coupled to the console;
  one or more accelerometers coupled to the console and;
  a valve configured to pass fluid therethrough, wherein the valve is configured to be decoupled from the container to dispose of fluid collected within the container;
 a fluid line coupled to the valve; and
 a container holder comprising:
  a sleeve configured to be secured to a user; and
  a pocket configured to securely hold the container,
 wherein the console includes one of more processors, a non-transitory storage medium, an energy source, and one or more logic modules configured to:
  receive accelerometer values from the one or more accelerometers;
  determine an acceleration state of the container; and
  activate the one or more ultrasonic sensors only when the acceleration state of the container is below a threshold; and
  measure a volume of voided urine over time in the container by measuring the volume when the acceleration state of the container is zero.

2. The automated UO-measuring system according to claim 1, wherein the console, the one or more ultrasonic sensors, the one or more accelerometers, and the valve are organized into a panel.

3. The automated UO-measuring system according to claim 2, wherein the panel divides the container into a proximal section and a distal section.

4. The automated UO-measuring system according to claim 3, wherein the panel is located at a proximal end or a distal end of the container.

5. The automated UO-measuring system according to claim 2, wherein the panel includes a pump configured to create a low-pressure environment inside the container.

6. The automated UO-measuring system according to claim 5, wherein the one or more logic modules are configured to:
receive ultrasonic sensor values from the one or more ultrasonic sensors;
correlate the ultrasonic sensor values with a volume-of-voided-urine value within the container and a time-of-day value for a correlation;
determine the volume of voided urine using the ultrasonic sensor values;
activate the pump to create and maintain the low-pressure environment inside the container;
transmit the correlation to a computing device; or
a combination thereof.

7. The automated UO-measuring system according to claim 6, wherein:
the pump includes a pressure sensor coupled with the console, and
the one or more logic modules are configured to:
receive pressure readings from the pressure sensor, and
activate the pump to create and maintain the low-pressure environment inside the container based on the pressure readings.

8. The automated UO-measuring system according to claim 1, wherein the container holder is configured to be detachably secured to the user.

9. The automated UO-measuring system according to claim 8, wherein the sleeve includes two or more arms configured to wrap around an appendage of the user.

10. The automated UO-measuring system according to claim 9, wherein the two or more arms are organized into a first pair of fastening arms and a first pair of securing arms.

11. The automated UO-measuring system according to claim 9, wherein the container holder is secured to the appendage of the user by hook-and-loop fasteners or magnets.

12. The automated UO-measuring system according to claim 1, wherein the sleeve includes a compression sock configured to be slidably secured to an appendage of the user.

13. The automated UO-measuring system according to claim 1, wherein the container is rigid.

14. The automated UO-measuring system according to claim 1, wherein the valve is configured to pass the fluid therethrough during collection of the fluid within the container.

15. A method of automatically measuring urine output, comprising:
capturing a volume of voided urine from a user, in a container using a fluid line,
the container being coupled to the user distal a bladder of the user,
the container configured to be held in a container holder, the container holder comprising:
a sleeve configured to be secured to the user; and
a pocket configured to securely hold the container;
wherein the container includes:
a valve configured to pass fluid therethrough, the valve configured to be decoupled from the container to dispose of fluid collected within the container; and
a console coupled to one or more ultrasonic sensors and one or more accelerometers;
detecting an acceleration state of the container;
measuring the volume of voided urine over time in the container;
correlating a measured volume of voided urine with a volume value and a time-of-day value; and
transmitting the volume value and the time-of-day value to a computing device,
wherein the console includes one of more processors, a non-transitory storage medium, an energy source, and one or more logic modules configured to:
receive accelerometer values from the one or more accelerometers;
determine the acceleration state of the container;
activate the one or more ultrasonic sensors only when the acceleration state of the container is below a threshold; and
wherein measuring the volume of voided urine over time in the container includes measuring the volume when the acceleration state of the container is zero.

16. The method according to claim 15, wherein capturing the volume of voided urine from the user includes maintaining a low-pressure environment in the container with a pump of the container.

17. The method according to claim 15, wherein detecting the acceleration state of the container includes using the one or more accelerometers to detect the acceleration state of the container.

18. The method according to claim 15, wherein measuring the volume of voided urine over time in the container includes using the one or more ultrasonic sensors to measure the volume of voided urine over time.

19. The method according to claim 15, wherein measuring the volume of voided urine over time in the container includes both measuring and recording at evenly spaced time intervals.

20. The method according to claim 19, wherein the evenly spaced time intervals are user-defined.

21. The method according to claim 15, wherein transmitting the volume value and the time-of-day value to the computing device includes wirelessly transmitting the volume value and the time-of-day value to the computing device.

* * * * *